United States Patent
Reed et al.

(10) Patent No.: US 11,306,128 B2
(45) Date of Patent: Apr. 19, 2022

(54) METHODS OF PURIFYING MUCIN

(71) Applicant: WISCONSIN ALUMNI RESEARCH FOUNDATION, Madison, WI (US)

(72) Inventors: Jess Dreher Reed, Verona, WI (US); Sergio Madrigal-Carballo, Ontario, CA (US); Michael Allen Polewski, Madison, WI (US); Christian Gerald Krueger, Cambridge, WI (US); Emilia Alfaro-Viquez, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 16/723,551

(22) Filed: Dec. 20, 2019

(65) Prior Publication Data
US 2020/0199185 A1 Jun. 25, 2020

Related U.S. Application Data

(60) Provisional application No. 62/783,894, filed on Dec. 21, 2018.

(51) Int. Cl.
| | |
|---|---|
| *A61K 38/00* | (2006.01) |
| *C07K 14/47* | (2006.01) |
| *C07K 1/36* | (2006.01) |
| *C07K 1/30* | (2006.01) |
| *C07K 1/14* | (2006.01) |

(52) U.S. Cl.
CPC .......... *C07K 14/4727* (2013.01); *C07K 1/145* (2013.01); *C07K 1/30* (2013.01); *C07K 1/36* (2013.01)

(58) Field of Classification Search
CPC ...... C07K 14/4727; C07K 1/145; C07K 1/30; C07K 1/36; C07K 1/006
See application file for complete search history.

(56) References Cited

U.S. PATENT DOCUMENTS 8,501,493 B2   8/2013   Combs et al.

FOREIGN PATENT DOCUMENTS

| JP | 05310799 A | * | 11/1993 | |
|---|---|---|---|---|
| JP | 2017145239 A | * | 8/2017 | |
| WO | WO-2007020889 A1 | * | 2/2007 | .............. A61P 31/04 |

OTHER PUBLICATIONS

Svensson et al. Layer-by-layer assembly of mucin and chitosan—Influence of surface properties, concentration and type of mucin. 2006. Journal of Colloid and Interface Science 299 (2006) 608-616 (Year: 2006).*
McGuckin et al. Methods and protocols—Mucin—ISSN 1064-3745 (Year: 2012).*
Arand, M., Friedberg, T., & Oesch, F. Colorimetric quantitation of trace amounts of sodium lauryl sulfate in the presence of nucleic acids and proteins. *Analytical biochemistry*. 1992. 207(1), 73-75.
Authimoolam SP, Dziubla TD. Biopolymeric Mucin and Synthetic Polymer Analogs: Their Structure, Function and Role in Biomedical Applications. *Polymers*. 2016. 8(3), 71.
Bansil R, Turner BS. Mucin structure, aggregation, physiological functions and biomedical applications. *Current Opinion in Colloid & Interface Science*. 2006. 11(2-3):164-170.
Goering & Van Soest. Forage Fiber Analyses (Apparatus, Reagents, Procedures, and Some Applications). *Agric. Handbook No. 379*. ARS-USDA, Washington, DC. 1970. pp. 8-11.
Medrum et al., Mucin gel assembly is controlled by a collective action of non-mucin proteins, disulfide bridges, $CA^{2+}$-mediated links, and hydrogen bonding, Scientific Reports, 2018, 8:5802.
Neutral Detergent Fiber (NDF), Apr. 2007. https://uwlab.triforce.cals.wisc.edu/wp-content/uploads/sites/17/2015/09/forage_NDF.pdf.

* cited by examiner

*Primary Examiner* — James H Alstrum-Acevedo
*Assistant Examiner* — Mercy H Sabila
(74) *Attorney, Agent, or Firm* — Daniel A. Blasiole; DeWitt LLP

(57) ABSTRACT

Methods of purifying mucin, purified mucin, and products comprising the purified mucin. The methods include combining a mucin-containing substance with water and one or more purification agents to form a purification mixture, incubating the purification mixture for a time sufficient to form a mucin precipitate in a liquid phase, and separating the mucin precipitate from the liquid phase. The purification agents include one or more of a surfactant, a chelating agent, and a protic solvent. The mucin purified from the methods can be used alone or in combination with a biopolymer such as a tannin and chitosan and can be used to generate materials in the form of a gel, a foam, a film, or a powder.

23 Claims, 9 Drawing Sheets

METHODS OF PURIFYING MUCIN

BACKGROUND

Mucins are a family of high molecular weight, heavily glycosylated proteins (glycoproteins) produced by epithelial or other tissues in most animals. Mucins make up 80-90% of the mucus that coats the surfaces of cells lining the respiratory, digestive, and urogenital tracts. Much of the rest of mucus is water, although mucus also contains small amounts of non-mucin protein (~1-2% w/w) and inorganic salts (~1% w/w). Mucins protect epithelial cells from infection, dehydration, and physical or chemical injury, as well as aid the passage of materials through a tract. Mucin 2 (MUC2, encoded by the MUC2 gene) is the most abundant mucin in the small intestine of mice, rats, swine, and humans.

Commercially available mucins are generally highly processed, which compromises their structure and properties. Mucin purification methods that preserve the structure and properties of mucins is needed.

FIELD OF THE INVENTION

The invention is directed to methods of purifying mucin, purified mucin, and products comprising purified mucin.

SUMMARY OF THE INVENTION

The present invention relates to rapid and inexpensive methods for purifying mucin from mucus. In an exemplary method, mucus is treated with a purification solution to solubilize non-mucin components of mucus and precipitate mucin. The mucin is then separated from the solubilized components by centrifugation or other methods. An exemplary purification solution comprises water and one or more purification agents selected from a surfactant, a chelating agent, and a protic solvent. In certain versions, the surfactant comprises sodium laurel sulfate, the chelating agent comprises ethylenediaminetetraacetic acid (EDTA), and the protic solvent comprises ethylene glycol monoethyl ether.

The methods of the invention are inexpensive and rapid and are suitable for the largescale commercial production of purified mucin, such as MUC2. The present method preserves mucin structure, including the disulfide bonds and oligosaccharides, which provide the high molecular weight and useful physical properties of mucin such as lubricity, gel-forming ability, and biological activity. This is in contrast to conventional mucin purification methods, which reduce the disulfide bonds that crosslink mucin, hydrolyze the mucin peptide bonds and oligosaccharides, and break down the mucin to peptides or small polysaccharide components, thus affecting overall bioactivity of mucin. The mucin purified with the methods of the invention maintain the ability to form hydrogels, which commercial mucin preparations cannot do. The mucin purified with the methods of the invention can be used in nutritional and biomedical applications.

The invention also relates to purified mucin made with the methods of the invention.

The invention also relates to materials made with the purified mucin of the invention.

The objects and advantages of the invention will appear more fully from the following detailed description of the preferred embodiment of the invention made in conjunction with the accompanying drawings.

DETAILED DESCRIPTION OF THE INVENTION

Figure 1:
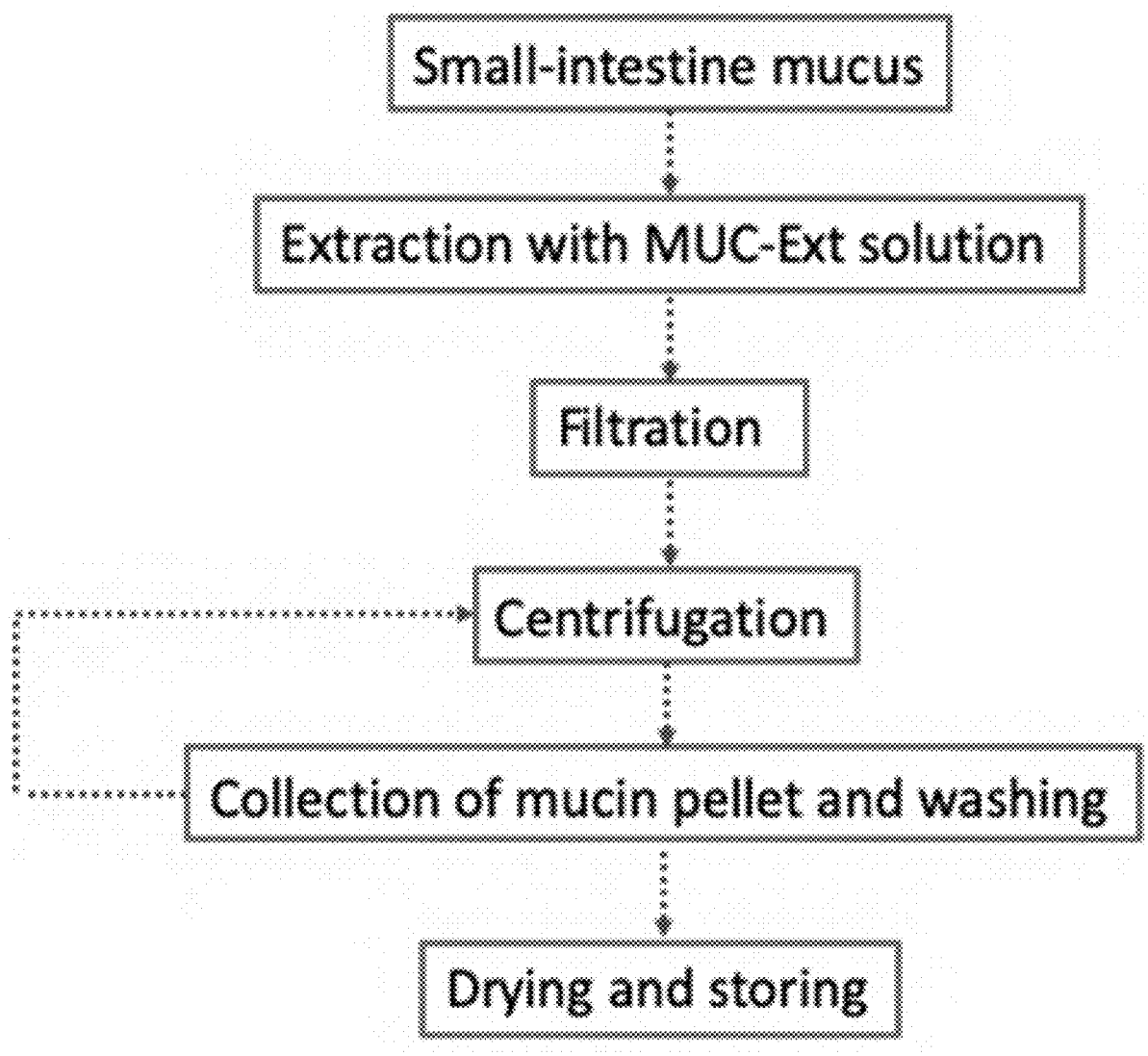
FIG. 1. Schematic representation of an exemplary method of the invention for purifying mucin from small intestine mucus.

One aspect of the invention is directed to methods of purifying mucin. The methods may comprise combining a mucin-containing substance with water and one or more purification agents to form a purification mixture and incubating the purification mixture for a time sufficient to form a mucin precipitate in a liquid phase. The mucin-containing substance is combined with amounts of the water and the one or more purification agents effective to form a mucin precipitate in a liquid phase. The purification agents may comprise one or more of a surfactant, a chelating agent, and a protic solvent. In some versions, the purification agents comprise each of a surfactant, a chelating agent, and a protic solvent. As used herein, "mucin precipitate" refers to mucin precipitated from a mucin-containing substance. The term can be used to refer to the mucin precipitated from the mucin-containing substance regardless of whether the mucin is subsequently washed, processed, combined with other materials or agents, solubilized, or formed into various forms.

Surfactants are amphiphilic compounds that comprise a hydrophilic head and a hydrophobic tail. The hydrophilic head may comprise a polar, nonionic head group or an ionic head group. The ionic head group may be an anionic head group, a cationic head group, or a zwitterionic (amphoteric) head group.

Nonionic surfactants are surfactants that have non-ionic head groups. The nonionic head groups may include hydroxyl groups or other polar groups. Examples of nonionic surfactants include long chain alcohols, such as cetyl alcohol, stearyl alcohol, cetostearyl alcohol (consisting predominantly of cetyl and stearyl alcohols), and oleyl alcohol; polyoxyethylene glycol alkyl ethers (Brij), such as those having the formula $CH_3-(CH_2)_{10-16}-(O-C_2H_4)_{1-25}-OH$, including octaethylene glycol monododecyl ether and pentaethylene glycol monododecyl ether, among others; polyoxypropylene glycol alkyl ethers, such as those having the formula $CH_3-(CH_2)_{10-16}-(O-C_3H_6)_{1-25}-O$; glucoside alkyl ethers, such as those having the formula $CH_3-(CH_2)_{10-16}-(O-Glucoside)_{1-3}-OH$, including decyl glucoside, lauryl glucoside, and octyl glucoside, among others; polyoxyethylene glycol octylphenol ethers, such as those having the formula $C_8H_{17}-(C_6H_4)-(O-C_2H_4)_{1-25}-OH$, including Triton X-100, among others; polyoxyethylene glycol alkylphenol ethers, such as those having the formula $C_9H_{19}-(C_6H_4)-(O-C_2H_4)_{1-25}-OH$, including nonoxynol-9, among others; glycerol alkyl esters, such as glyceryl laurate, among others; polyoxyethylene glycol sorbitan alkyl esters, such as polysorbate, among others; sorbitan alkyl esters, such as Spans, among others; cocamide MEA; cocamide DEA; codecyldimethylamine oxide; block copolymers of polyethylene glycol and polypropylene glycol, such as poloxamers, among others; and polyethoxylated tallow amine (POEA).

Anionic surfactants are surfactants that have anionic head groups. The anionic head groups may include sulfate, sulfonate, phosphate, and/or carboxylate groups, among others. Examples of anionic surfactants include alkyl sulfates, such as ammonium lauryl sulfate, sodium lauryl sulfate (SDS, sodium dodecyl sulfate), alkyl-ether sulfates such as sodium laureth sulfate, and sodium myreth sulfate, among others. Examples of anionic surfactants also include sulfonates, such as sodium dodecyl sulfonate, dioctyl sodium sulfosuccinate, perfluorooctanesulfonate (PFOS), perfluorobutanesulfonate, and linear alkylbenzene sulfonates (LABs), among others. Carboxylates are preferred surfactants. Carboxylates comprise alkyl carboxylates, such as fatty acids and salts thereof. Examples of carboxylates include sodium stearate, sodium lauroyl sarcosinate, and carboxylate-based fluorosurfactants, such as perfluorononanoate, and perfluorooctanoate (PFOA or PFO). Preferred anionic surfactants include cocoyl isethionate, sodium dodecylbenzinesulfonate, and sodium isethionate.

Cationic surfactants are surfactants that have cationic head groups. The cationic head groups may include pH-dependent primary, secondary, or tertiary amines and permanently charged quaternary ammonium cations, among others. Primary amines become positively charged at pH<10, secondary amines become positively charged at pH<4. An example of a pH-dependent amine is octenidine dihydrochloride. Permanently charged quaternary ammonium cations include alkyltrimethylammonium salts, such as cetyl trimethylammonium bromide (CTAB, hexadecyl trimethyl ammonium bromide), cetyl trimethylammonium chloride (CTAC), cetylpyridinium chloride (CPC), benzalkonium chloride (BAC), benzethonium chloride (BZT), 5-Bromo-5-nitro-1,3-dioxane, dimethyldioctadecylammonium chloride, cetrimonium bromide, and dioctadecyldimethylammonium bromide (DODAB), among others.

Zwitterionic (amphoteric) surfactants are surfactants that have zwitterionic head groups. Zwitterionic head groups include both cationic and anionic centers. The cationic center may be based on primary, secondary, or tertiary amines, quaternary ammonium cations, or others. The anionic part may include sulfonates, as in CHAPS (3-[(3-Cholamidopropyl)dimethylammonio]-1-propanesulfonate), or sultaines, as in cocamidopropyl hydroxysultaine. Other examples of zwitterionic head groups include betaines, such as cocamidopropyl betaine, and choline-phosphates, such as those occurring in lecithin, among others.

For ionic head groups, the counter-ion can be monoatomic/inorganic or polyatomic/organic. Monoatomic/inorganic cationic counter-ions include metals, such as the alkali metals, alkaline earth metals, and transition metals. Monoatomic/inorganic anionic counter-ions include the halides, such as chloride (Cl—), bromide (Br—), and iodide (I—). Polyatomic/organic cationic counter-ions include ammonium, pyridinium, and triethanolamine (TEA), among others. Polyatomic/organic anionic counter-ions include tosyls, trifluoromethanesulfonates, and methylsulfate, among others.

The hydrophobic tail of the surfactant may include a linear, branched, or aromatic hydrocarbon chain. The hydrocarbon chain may have any number of carbon atoms suitable to render it hydrophobic. The number of carbon atoms may include from 9 to 30 carbon atoms, from 10 to 20 carbon atoms, or from 12 to 18 carbon atoms. Such carbon atoms may be saturated, unsaturated, straight-chained, branched, or cyclic. The hydrocarbon chain may be substituted with one or more heteroatoms.

Preferred surfactants for use in the present methods include anionic surfactants, nonionic surfactants, and zwitterionic surfactants, such as ammonium lauryl sulfate, laureth sulfate, lauroyl sarcosinate, sodium laurylsulfonate, and lauryl glucoside. Particularly preferred surfactants include anionic surfactants, such as ammonium lauryl sulfate, laureth sulfate, lauroyl sarcosinate, and sodium laurylsulfonate.

Chelating agents are compounds that form coordinate covalent bonds with metal ions to form stable, water-soluble metal complexes. Chelating agents are well known in the art. Chelating agents are sometimes referred to as "metal chelators," "chelants," "chelators," and "sequestering agents"

Exemplary chelating agents include acetylacetone, alizarin, amidoxime, amidoxime group, aminoethylethanolamine, aminomethylphosphonic acid, aminopolycarboxylic acid, aminotris(methylenephosphonic acid) (ATMP), 1,2-bis(o-aminophenoxy)ethane-N,N,N',N'-tetraacetic acid (BAPTA), bathocuproine, BDTH2, benzotriazole, bidentate, bipyridine, 2,2'-bipyridine, 2,2'-bipyrimidine, bis(dicyclohexylphosphino)ethane, 1,2-bis(dimethylarsino)benzene, 1,2-bis(dimethylphosphino)ethane, 1,4-bis(diphenylphosphino)butane, 1,2-bis(diphenylphosphino)ethane, calixarene, carcerand, catechol, cavitand, chelating resin, Chelex 100, citrate, citric acid, clathrochelate, corrole cryptand, 2.2.2-cryptand, cyclam, cyclen, cyclodextrin, deferasirox, deferiprone (1,2-dimethyl-3-hydroxypyrid-4-one), deferoxamine, denticity, desferrioxamine (deferoxamine, DFO), dexrazoxane, diacetyl monoxime, trans-1,2-diaminocyclohexane, 1,2-diaminopropane, 1,5-diaza-3,7-diphosphacyclooctanes, 1,4-diazacycloheptane, dibenzoylmethane, diethylenetriamine, diglyme, 2,3-dihydroxybenzoic acid, dimercaprol (2,3-dimercapto-1-propanol), 2,3-dimercapto-1-propanesulfonic acid, dimercaptosuccinic acid, 1,2-dimethylethylenediamine, 1,1-dimethylethylenediamine, dimethylglyoxime, disodium ethylenediaminetetraacetate dehydrate, 2,3-O-isopropylidene-2,3-dihydroxy-1,4-bis (diphenylphosphino)butane (DIOP), diphenylethylenediamine, 1,5-dithiacyclooctane, domoic acid, DOTA (also known as tetraxetan), DOTA-TATE (also known as DOTA-octreotate, oxodotreotide, and DOTA-(Tyr$^3$)-octreotate/DOTA-O-Tyr$^3$-octreotate), diethylenetriamine pentaacetic acid, diethylenetriamine penta(methylene phosphonic acid) (DTPMP), ethylenediamine, ethylenediamine-N,N'-bis(2-hydroxyphenylacetic acid) (EDDHA), ethylenediamine-N,N'-disuccinic acid (EDDS), ethylenediaminetetraacetic acid (EDTA), ethylenediamine tetra(methylene phosphonic acid) (EDTMP), ethylene glycol tetraacetic acid (EGTA), ethylene glycol-bis(β-aminoethyl ether)-N,N,N',N'-tetraacetic acid, 1,2-ethanedithiol, ethylenediaminediacetic acid (EDDA), etidronic acid, fluo-4, fura-2, gallic acid, gluconic acid, glutamic acid, glyoxal-bis (mesitylimine), glyphosate, hexafluoroacetylacetone, homocitric acid, 3-hydroxypyridin-4-ones, iminodiacetic acid, indo-1, isosaccharinic acid, kainic acid, malic acid, metal acetylacetonates, metal dithiolene complex, metallacrown, nitriloacetic acid, nitrilotriacetic acid, oxalic acid, oxime, pendetide, penicillamine, pentetic acid, phanephos, phenanthroline, O-phenylenediamine, phosphonate, phthalocyanine, phytochelatin, picolinic acid, polyaspartic acid, polystyrene sulfonates, porphine, porphyrins, 3-pyridylnicotinamide, 4-pyridylnicotinami de, pyrogallol, salicylic acid, sarcophagine, sodium citrate, sodium diethyldithiocarbamate, sodium polyaspartate, terpyridine, tetramethylethylenediamine, tetraphenylporphyrin, thenoyltrifluoroacetone, thioglycolic acid, N,N,N',N'-tetrakis(2-pyridinylmethyl)-1,2-ethanediamine (TPEN), 1,4,7-triazacyclononane, tributyl phosphate, tridentates, triethylenetetramine, 1,1,1-trifluoroacetylacetone, 1,4,7-trimethyl-1,4,7-triazacyclononane, triphos, trisodium citrate, 1,4,7-trithiacyclononane, and thenoyltrifluoroacetone (TTFA), among others. Preferred chelating agents include at least one of ethylenediaminetetraacetic acid, disodium ethylenediaminetetraacetate dehydrate, nitriloacetic acid, and diethylenetriamine pentaacetic acid.

Protic solvents include compounds containing at least one hydrogen atom connected directly to an electronegative atom (such as 0 or N). Protic solvents include solvents having the ability to be a hydrogen bond donor. Protic solvents are well known in the art. Exemplary protic solvents include alcohols, amides, amines, and other compounds. Exemplary protic solvents include ammonia, acetic acid, hydrogen fluoride, formic acid, nitromethane, and alcohols. Exemplary alcohols include tert-amyl alcohol, benzyl alcohol, 1,4-butanediol, 1,2,4-butanetriol, butanol, 2-butanol, n-butanol, tert-butyl alcohol, denatured alcohol, di(propylene glycol) methyl ether, diethylene glycol, diethylene glycol dimethyl ether, ethanol, ethylene glycol, ethylene glycol monoethyl ether, 2-ethylhexanol, furfuryl alcohol, glycerol (glycerine/glycerin), isobutanol, isopropyl alcohol, methanol, 2-(2-methoxyethoxy)ethanol, 2-methyl-1-butanol, 2-methyl-1-pentanol, 3-methyl-2-butanol, neopentyl alcohol, 2-pentanol, 1,3-propanediol, 1-propanol, 2-propanol, propylene glycol, propylene glycol methyl ether, and triethylene glycol, among others. Preferred protic solvents include alcohols, such as one or more of ethylene glycol monoethyl ether, propylene glycol, and glycerin.

The incubating can be conducted for any time sufficient to form the mucin precipitate in the liquid phase. The incubating in some versions is conducted for at least about 1 minute, at least about 5 minutes, at least about 5 minutes, at least about 10 minutes, at least about 20 minutes, at least about 30 minutes, at least about 40 minutes, at least about 50 minutes, at least about 60 minutes, at least about 70 minutes, at least about 80 minutes, or at least about 90 minutes. The incubating in some versions is conducted up to about 30 minutes, up to about 40 minutes, up to about 50 minutes, up to about 60 minutes, up to about 70 minutes, up to about 80 minutes, up to about 90 minutes, up to about 100 minutes, or more.

The incubating is preferably conducted at a temperature of about 0-90° C. The incubating in some versions is conducted at a temperature of at least about 0° C., at least about 5° C., at least about 10° C., at least about 15° C., or at least about 20° C. The incubating in some versions is conducted at a temperature up to about 30° C., up to about 35° C., up to about 40° C., up to about 45° C., up to about 50° C., up to about 55° C., up to about 60° C., up to about 65° C., up to about 70° C., up to about 75° C., up to about 80° C., up to about 85° C., or up to about 90° C.

The incubating in some versions comprises mixing the purification mixture. The mixing can comprise intermittent mixing or constant mixing. Exemplary ways of mixing include stirring, swirling, rotating, and vortexing.

In some versions of the invention, the combining comprises combining the mucin-containing substance with a purification solution comprising the water and the one or more purification agents. The purification solution may comprise any one or more of the surfactant, the chelating agent, and the protic solvent in any amounts.

The surfactant is preferably included in the purification solution in an amount from about 0.001% w/v, about 0.003% w/v, about 0.01% w/v, about 0.03% w/v, about 0.1% w/v, about 0.3% w/v, about 1% w/v, about 3% w/v or more to about 0.003% w/v, about 0.01% w/v, about 0.03% w/v, about 0.1% w/v, about 0.3% w/v, about 1% w/v, about 3% w/v, about 10% w/v, about 3% w/v, about 10% w/v or more. Exemplary ranges include about 0.1-30% w/v, such as about 0.3-10% w/v or about 1-3% w/v The chelating agent is preferably included in the purification solution in an amount from about 0.001% w/v, about 0.003% w/v, about 0.01% w/v, about 0.03% w/v, about 0.1% w/v, about 0.3% w/v, about 1% w/v, about 3% w/v or more to about 0.003% w/v, about 0.01% w/v, about 0.03% w/v, about 0.1% w/v, about 0.3% w/v, about 1% w/v, about 3% w/v, about 10% w/v, about 3% w/v, about 10% w/v or more. Exemplary ranges include about 0.1-20% w/v, such as about 0.3-6% w/v or about 1-2% w/v.

The protic solvent is preferably included in the purification solution in an amount from about 0.001% v/v, about 0.003% v/v, about 0.01% v/v, about 0.03% v/v, about 0.1% v/v, about 0.3% v/v, about 1% v/v, about 3% v/v or more to about 0.003% v/v, about 0.01% v/v, about 0.03% v/v, about 0.1% v/v, about 0.3% v/v, about 1% v/v, about 3% v/v, about 10% v/v, about 3% v/v, about 10% v/v or more. Exemplary ranges include about 0.05-15% v/v, such as about 0.2-5% v/v or about 0.5-1.5% v/v.

The water is preferably included in the purification solution in an amount greater than about 50% v/v, greater than about 55% v/v, greater than about 60% v/v, greater than about 65% v/v, greater than about 70% v/v, greater than about 75%, v/v, greater than about 80% v/v, greater than about 85% v/v, greater than about 90% v/v, greater than about 95% v/v, greater than about 99% or more.

The purification solution preferably has a pH from about 5, about 5.5, about 6, about 6.5, or about 7 to about 6, about 6.5, about 7, about 7.5, about 8, or about 8.5. Exemplary pH ranges include from about 6 to about 8, such as from about 6.5 to about 7.5.

The purification solution preferably comprises one or more buffering agents. Buffering agents suitable for maintaining various pH ranges are well known in the art. Examples include borates such as sodium borate decahydrate and boric acid; carbonates such as ammonium carbonate, calcium carbonate, sodium carbonate, and bicarbonate; citrates such as citric acid (trisodium dehydrate, dibasic ammonium salt); glycine; phosphates such as ammonium phosphate dibasic, potassium phosphate dibasic anhydrous, potassium phosphate monobasic, potassium phosphate tribasic, sodium phosphate dibasic heptahydrate, and disodium hydrogenphosphate anhydrous; and tris, among others. An exemplary form of the invention comprises sodium borate decahydrate and disodium hydrogen phosphate.

The purification solution can be combined with the mucin-containing substance in any ratio that results in a mucin precipitate. Exemplary ratios include a volume ratio (vol. mucin-containing substance:vol. purification solution) of from about 1000:1 to about 1:1000, such as about 500:1 to about 1:500, about 100:1 to about 1:100, or about 50:1 to about 1:50, or about 10:1 to about 1:10. In some versions the volume ratio is about 1:10 (vol. mucin-containing substance: vol. purification solution).

The mucin-containing substance can include any substance comprising mucin and at least one non-mucin component. Various exemplary non-mucin components include liquids such as water, non-mucin proteins, and inorganic salts. The non-mucin proteins can include immunoglobulins, enzymes (such as lysozymes), glycoproteins such as lactoferrin, and other types of proteins. The inorganic salts can include salts of sodium, potassium, magnesium, or calcium and can include chloride or other counterions. The salts may be dissociated and dissolved within the mucin-containing substance. The mucin-containing substance may be in a solid form, a semi-solid form (e.g., gel, foam), or a liquid form. In some versions, the mucin-containing substance is mucus or processed forms thereof. The mucus can be obtained from any natural source. Exemplary sources include the respiratory (e.g., lungs), gastrointestinal (e.g., small intestine, including duodenum and jejunum), urogenital, visual, and auditory systems of animals. Exemplary animals include mammals. Exemplary mammals include pigs, cattle, goats, and sheep. Methods for obtaining mucus from such sources are well known in the art and include scraping the inner lumen of the intestines, among other methods. Accordingly, the mucin-containing substance in some versions comprises one or more of water, non-mucin protein, and inorganic salts. The mucin-containing substance in some versions is a gel. The mucin containing substance in some versions comprises mucus. The mucin-containing substance in some versions comprises intestinal mucus.

Once the mucin-containing substance is combined with the purification agents (such as in the purification solution) and the mucin precipitate is formed in the liquid phase, the mucin precipitate can be separated from the liquid phase. Various separation methods include centrifugation and/or filtration, among others. In some versions, the separating comprises centrifuging the mucin precipitate in the liquid phase to form a mucin precipitate pellet and a liquid phase supernatant and removing the liquid phase supernatant from the mucin precipitate pellet. In some versions, the mucin precipitate pellet comprises a first fraction and a second fraction, wherein the first fraction is denser than the second fraction. The first fraction comprises at least one of tissue, surfactant, and lipids. The second fraction comprises the mucin precipitate. In some versions, the method further comprises separating the first fraction from the second fraction and retaining the second fraction for downstream processing or direct applications.

The mucin precipitate pellet can optionally be washed one or more times with a wash solution before further use, or can be used directly.

In some versions, the mucin precipitate is washed with a water-based wash solution. In some versions, the water-based wash solution comprises any one or more of the purification agents. In some versions, the water-based wash solution comprises the purification solution.

In some versions, the water-based wash solution is an acidic wash solution. As used herein, "acidic wash solution" refers to a water-based wash solution having a pH less than 7. In some versions, the acidic wash solution has a pH no greater than about 6.5, no greater than about 6, no greater than about 5.5, no greater than about 5, or no greater than about 4.5. In some versions, the acidic wash solution has a pH of at least about 1, at least about 1.5, at least about 2, at least about 2.5, at least about 3, or at least about 3.5. In some versions, the acidic wash solution has a pH of about 4. The acidic wash solution can comprise water and an acid. Exemplary acids include hydrochloric acid (HCL), sulfuric acid ($H_2SO_4$), nitric acid ($HNO_3$), carbonic acid ($H_2CO_3$), uric acid, ascorbic acid, citric acid, acetic acid, among others. In some versions, the acidic wash solution further comprises a buffer. In some versions, the acidic wash solution further comprises salts.

In some versions, the mucin precipitate is washed with an organic solvent. Exemplary organic solvents include acetone; alcohols, including aliphatic alcohols, such as methanol, ethanol, isopropanol, etc.; and acetonitrile, among others. Washing the mucin precipitate with an organic solvent such as acetone is unexpectedly effective in removing residual surfactant associated with the mucin precipitate after precipitation from the mucin-containing sub stance.

The above-described washes can be conducted by mixing or suspending the mucin precipitate with the wash solution followed by separating the mucin precipitate from the wash solution. The separation can be conducted using any separation method described herein. An exemplary separation methods include centrifugation and filtration. As with separating the mucin precipitate from the liquid phase of purification agents, centrifugation may result in a pellet having a dense fraction and a less-dense fraction. In such a case, separation of the dense fraction and the less-dense fraction and retention of the less-dense fraction is preferred.

Any combination of the washes described above can be carried out. In some versions, one or more washes with an acidic wash solution is followed by one or more washes with an organic solvent.

The washes are preferably performed to an extent such that the mucin precipitate contains very low amounts of surfactant after the washing. In some versions, the washed mucin precipitate includes, by dry weight of the mucin precipitate, no more than about 0% w/w, no more than about 0.001% w/w, no more than about 0.01% w/w, no more than about 0.1% w/w, no more than about 0.5% w/w, no more than about 1% w/w, no more than about 1.5% w/w, no more than about 2% w/w, no more than about 2.5% w/w, no more than about 3% w/w, no more than about 3.5% w/w, no more than about 4% w/w, no more than about 4.5% w/w, or no more than about 5% w/w of residual surfactant.

Any separation step described herein, whether separating the mucin precipitate from the liquid phase of purification agents or the wash solution, can be performed at a temperature above 0° C. and less than 20° C. In some versions, the separating is conducted at a temperature less than about 20° C., less than about 15° C., less than about 10° C., or less than about 5° C. In some versions, the separating is conducted at a temperature greater than about 0° C.

After separation from the liquid phase of purification agents or from the wash solution, the mucin precipitate can be dried. The drying can be performed by air drying or by freeze-drying (lyophilization).

The resulting purified mucin can have a reduced amount of one or more of the non-mucin components originally present in the mucin-containing substance. In some versions, the purified mucin includes, by dry weight of the purified mucin, no more than about 0% w/w, no more than about 0.001% w/w, no more than about 0.01% w/w, no more than about 0.1% w/w, or no more than about 0.5% w/w non-mucin protein. In some versions, the purified mucin includes, but dry weight of the purified mucin, no more than about 0% w/w, no more than about 0.001% w/w, no more than about 0.01% w/w, no more than about 0.1% w/w, or no more than about 0.5% w/w inorganic salt. In some versions, the purified mucin contains less than about 1% by weight, less than about 5% by weight, less than about 10% by weight, less than about 15% by weight, less than about 20% by weight, less than about 25% by weight, less than about 30% by weight, less than about 35% by weight, less than about 40% by weight, less than about 50% by weight, less than about 55% by weight, less than about 60% by weight, less than about 65% by weight, less than about 70% by weight, less than about 75% by weight, less than about 80% by weight, less than about 85% by weight, less than about 90% by weight, less than about 95% by weight, or less than about 99% by weight non-mucin protein than an amount of non-mucin protein present in the mucin-containing substance. In some versions, the purified mucin contains less than about 1% by weight, less than about 5% by weight, less than about 10% by weight, less than about 15% by weight, less than about 20% by weight, less than about 25% by weight, less than about 30% by weight, less than about 35% by weight, less than about 40% by weight, less than about 50% by weight, less than about 55% by weight, less than about 60% by weight, less than about 65% by weight, less than about 70% by weight, less than about 75% by weight, less than about 80% by weight, less than about 85% by weight, less than about 90% by weight, less than about 95% by weight, or less than about 99% by weight inorganic salt than an amount of inorganic salt present in the mucin-containing substance.

The purified mucin can comprise or consist of covalently bound (e.g., via disulfide bonds) mucin complexes having a mass of from about 400 kDa, about 500 kDa, about 750 kDa, about 1,000 kDa, about 1,500 kDa, about 2000 kDa, about 2,500 kDa, about 3,000 kDa, about 4,000 kDa, about 5,000 kDa, about 7,500 kDa, about 10,000 kDa, about 15,000 kDa, about 20,000 kDa, about 25,000 kDa, about 30,000 kDa or more to about 500 kDa, about 750 kDa, about 1,000 kDa, about 1,500 kDa, about 2000 kDa, about 2,500 kDa, about 3,000 kDa, about 4,000 kDa, about 5,000 kDa, about 7,500 kDa, about 10,000 kDa, about 15,000 kDa, about 20,000 kDa, about 25,000 kDa, about 30,000 kDa, about 32,000 kDa or more.

The purified mucin can comprise or consist of mucin complexes comprising individual mucin polypeptide chains (individual polypeptide backbones) covalently bound to each other via disulfide bonds.

The purified mucin can comprise glycosylated mucin. The glycosylated mucin can comprise oligosaccharide side chains. The oligosaccharide chains can be covalently bound to the mucin polypeptide backbone via 0-glycosidic linkages.

The purified mucin can comprise any of the characteristics of mucins found in native mucus as described in Authimoolam et al. (Authimoolam S P, Dziubla T D. Biopolymeric Mucin and Synthetic Polymer Analogs: Their Structure, Function and Role in Biomedical Applications. *Polymers*, 2016, 8(3), 71), which is incorporated herein by reference in its entirety. These characteristics include oligomerization of various mucin polypeptide backbones (e.g., dimers, trimers, tetramers, mucin networks, etc.), backbone-backbone covalent bonds (e.g., disulfide bonds), and glycosylation (e.g., O-glycosylation), among others.

The purified mucin can comprise Mucin 2 (MUC2).

The purified mucin can be in the form of a gel, a powder, a foam, or a film, among others.

The resulting purified mucin can be used in any of a number of applications. The purified mucin, for example, can be used to generate a gel by mixing with water and, optionally, other additional components. The purified mucin can be used to generate a foam by mixing with water and, optionally, other additional components, followed by freeze drying the mixture. The purified mucin can be used to generate a film by mixing with water and, optionally, other additional components, followed by partially dehydrating the mixture. The other additional components can include biopolymers. Exemplary biopolymers include chitosan, tannins (hydrolysable tannins, condensed tannins), lignin, nucleic acids (DNA, RNA), polypeptides, etc. The biopolymers can crosslink or non-covalently associate with the mucin and stabilize the materials made therewith.

The films can serve as coatings on surfaces. The surface can be a surface of a medical device. "Medical device" in this context refers to any device configured to and/or intended to enter, be implanted in, or directly contact a mammalian body. Non-limiting examples of medical devices include pacemakers, syringes, catheters, thermometers, sutures, scalpels, dressings, intrauterine devices, tracheal tubes, gauze, insulin pumps, feeding tubes, adhesive bandages, surgical mesh, elastic bandages, gastric bands, speculums, and stents, among others. The purified mucin is preferably coated on a portion of the medical device that contacts a portion of the mammalian body. The medical device can be plastic, metal, made of organic materials, or a combination thereof.

The purified mucin of the invention may also be used as a glycosaminoglycan supplement for use in cystitis. For example, the purified mucin of the invention could be instilled as a gel into the bladder or urogenital tract via catheter. Interstitial cystitis/bladder pain syndrome (IC/BPS) is thought to be caused by a disruption of the mucosal bladder surface layer, leading to a loss or alteration of glycosaminoglycans (GAGs), a class of molecules that repel water. When GAGs are not present, the bladder wall may be penetrated by substances that trigger an inflammatory response. Replenishment of the GAG layer helps this condition. Key treatments that help achieve GAG replenishment include heparin, chondroitin sulfate, pentosan polysulphate, hyaluronic acid, and a combination of chondroitin sulphate and hyaluronic acid. The purified mucin of the invention can be used as a replacement for—in combination with—these agents for GAG replenishment.

The purified mucin of the invention may also be used as a dietary supplement or intestinal mucosal replacement (similar to GAG supplement as described above). In this use, the purified mucin of the invention can be consumed orally to replenish or repair a damaged mucosal barrier in the gut.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

EXAMPLES

Extraction and Purification of Mucin from Swine Small Intestines for Nutritional and Biomedical Applications Example 1. Background Mucins are a family of high molecular weight, heavily glycosylated proteins (glycoproteins) produced by epithelial tissues in most animals. See Bansil et al. (Bansil R, Turner B S. Mucin structure, aggregation, physiological functions and biomedical applications. Current Opinion in Colloid & Interface Science, 2006, 11(2-3):164-170) and Authimoolam et al. (Authimoolam S P, Dziubla T D. Biopolymeric Mucin and Synthetic Polymer Analogs: Their Structure, Function and Role in Biomedical Applications. Polymers, 2016, 8(3), 71) for structural and functional aspects of mucins. Mucins are a critical component of the mucus that coats the surfaces of cells lining the respiratory, digestive, and urogenital tracts. Mucus protects epithelial cells from infection, dehydration, and physical or chemical injury, as well as aids the passage of materials through a tract. Mucin 2 (MUC2, encoded by the MUC2 gene) is the most abundant mucin in the small intestine of mice, rats, swine and humans. Unlike other types of mucin, the high molecular weight of MUC2 (estimates are from 2 to 10 MDa or more) gives it properties that make it ideal for development as a valuable co-product from the processing of swine for pork production or other animals.

The function of mucins in vivo is dependent on their ability to form viscous solutions or gels. The highly glycosylated domains of mucins are devoid of secondary structure and are long, extended structures that are much less flexible than un-glycosylated random coils. The oligosaccharides contribute to this stiffness by limiting the rotation around peptide bonds and by inducing charge repulsion among the neighboring, negatively charged oligosaccharide groups. Such long, extended molecules have a much greater solution volume than native or denatured proteins with little or no carbohydrate and endow aqueous mucin solutions with a high viscosity. Mucins protect against infection by microorganisms that bind cell surface carbohydrates, and mucin genes appear to be upregulated by substances derived from bacteria, such as lipopolysaccharides.

Native mucin has shown promising properties that could be very valuable for biomedical applications. These include the adsorption onto and lubrication of surfaces, among others. Although mucins are commercially available (Sigma Aldrich, Fisher), various studies have found that the commercial mucins cannot reproduce the properties of native mucins. Commercial mucins, for example, do not form hydrogels and are inferior in inhibiting virus infection compared to natively purified mucins. Traditional methods of purifying mucin for mucin extraction involve hydrolysis of the mucin, thereby breaking down mucin macrostructure into peptides or small polysaccharide components, and this could affect the overall bioactivity of mucin.

The present examples show a rapid and inexpensive method for purifying mucin in a manner that preserves the properties of native mucin. FIG. 1 shows a general schema outlining the method. The method involves only two basic steps using solvent extraction and precipitate separation techniques. The first step involves combining mucus with a purification solution to precipitate mucin. The second step involves separating the precipitated mucin from the non-precipitated components using one or more separation techniques such as centrifugation. The two basic steps can be repeated one or more times to wash the purified mucin, and the resulting purified mucin can be freeze dried or used immediately in any of a number of applications. The mucin purified with the present methods maintains the desired properties of mucin, such as lubricity, gel-forming ability, selective binding of molecules, and other biological activity and can be used for nutritional and biomedical applications.

Example 2. Preparation of Mucin Extracting Solution (MUC-Ext)

A purification solution, referred to in the present examples as "Mucin Extracting Solution" or "MUC-Ext," was prepared according the formula provided in Table 1.

TABLE 1

Master Formula for Preparation of Mucin Extracting Solution (MUC-Ext)*.

| Ingredient | Composition in (1000 mL) |
| --- | --- |
| Sodium laurel sulfate | 10-30 g |
| Ethylenediamine tetracetic acid | 10-20 g |
| Sodium hydroxide | 3-10 g |
| Sodium borate decahydrate | 3-10 g |
| Disodium hydrogen phosphate | 1-5 g |
| Ethylene glycol mono ethyl ether | 5-15 g |
| Water | To complete volume |

*pH of solution regulated to 7.0. EDTA and NaOH can be replaced by EDTA disodium salt (5-20 g).

To prepare the Mucin Extracting Solution, the EDTA and sodium borate were placed together in a large beaker with some of the distilled water and were heated until dissolved. The sodium lauryl sulfate and ethylene glycol mono ethyl ether were then added to the solution. The disodium hydrogen phosphate was then added in a separate beaker with some of the distilled water, heated until dissolved, and then added to the solution containing other ingredients. The pH was checked and adjusted as necessary with NaOH or HCl to be within a range of 6.9 to 7.1. If the solution is properly made, pH adjustment is rarely required. See, e.g., Goering & Van Soest (1970) Forage Fiber Analyses (Apparatus, Reagents, Procedures, and Some Applications) Agric. Handbook No. 379, pp. 8-11, ARS-USDA, Washington, D.C.

Example 3. Purification of Mucin from Swine Small Intestine Mucus with the Mucin Extracting Solution Mucin was isolated from swine small intestine mucus with the Mucin Extracting Solution. Swine small intestines were obtained from a local abattoir, placed on ice, and transported back to the lab for processing. The small intestines were cut into 1-meter sections. Each section was cut longitudinally and laid flat to expose the lumen of the intestine. Using a spatula/putty knife, the mucosal surface of each section was lightly scraped to obtain mucus, and the mucus was collected into a beaker. Materials from multiple intestinal sections were pooled together.

Once sufficient material was collected, the mucus was combined with Mucin Extracting Solution (MUC-Ext) (Table 1) at a ratio of 1:10 (vol. mucus:vol. MUC-Ext) and allowed to mix on an orbital shaker for 1 hour at room temperature to ensure sufficient mixing.

After the 1 hour of mixing, the mixed material was poured through a sieve (i.e., cheesecloth) to separate out lipid material and any remaining digesta/chime.

The filtered, mixed material was then aliquoted into tubes (40 mL/tube) and centrifuged at 11,000×g for 60 minutes at 4° C. After centrifugation, the supernatant was discarded, and the pellet was washed 3 times using 40 mL of Mucin Extracting Solution and centrifugation as outlined above for the original purification. Pellets from multiple tubes were dislodged with a spatula, pooled together, and vortexed to ensure a homogenous mixture. The pooled material was frozen at −20° C. and then subjected to lyophilization. This freeze-dried material was used in further analysis and for the formulation of foams, films, and wound dressings.

Figure 2:
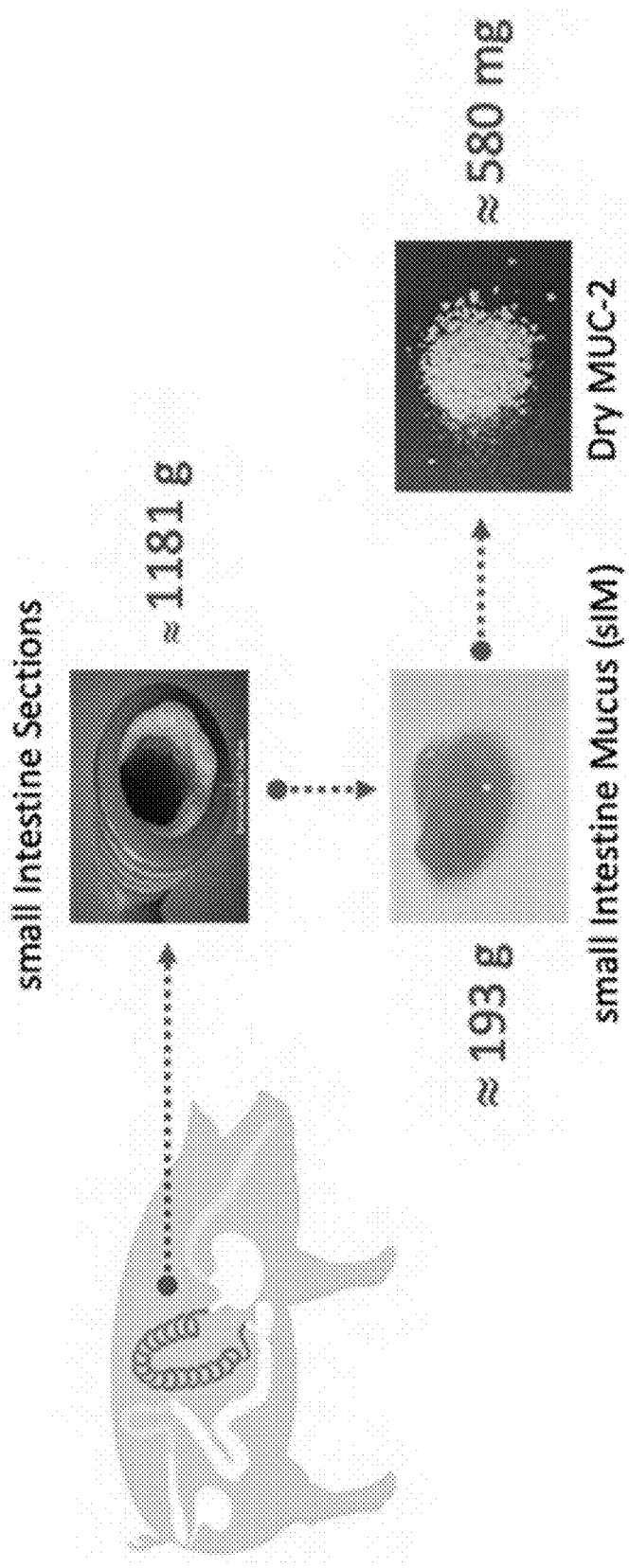
FIG. 2. Schematic illustration of mucin extraction yield per pig small intestine using an exemplary method of the invention.
Figure 3:
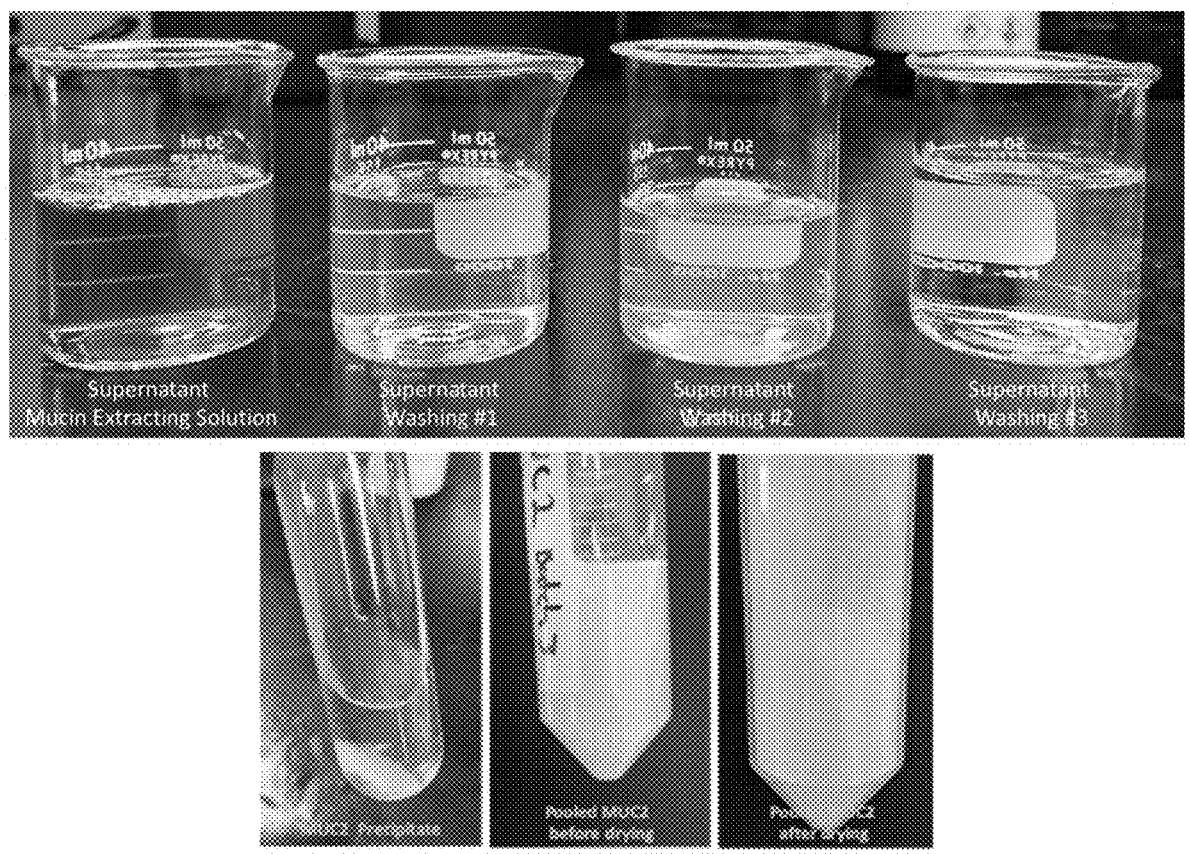
FIG. 3. Photographs depicting the extraction and purification of MUC2 from pig small intestine at various stages in an exemplary method of the invention.
Figure 4:
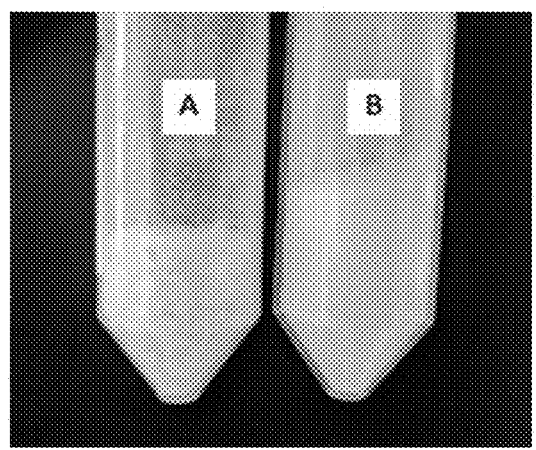
FIG. 4. Images depicting the normal physical appearance of mucin: (A) Reagent grade porcine stomach mucin obtained from Sigma-Aldrich (St. Louis, Mo.; Cat. No. M1778-10G, Batch No. 064K7005); (B) Porcine small intestine mucin isolated from the small intestine.

The yield of the dry mucin from the scraped mucus was about 0.3% w/w (FIG. 2). The physical appearance of various materials at various stages of the purification process is shown in FIG. 3. The materials include the centrifugation supernatants after the initial extraction and after each of three washings, the mucin pellet after the initial centrifugation, the pooled mucin prior to drying, and the pooled mucin after drying. The physical appearance of commercial porcine stomach mucin (A) compared to the purified small intestine mucin (B) of the invention is shown in FIG. 4.

Example 4. Characterization of the Purified Mucin

The purified mucin from the Example 3 was characterized using a number of different assays.

Figure 5:
FIG. 5. Identification of mucin domains in commercial porcine stomach mucin (Ref-Mucin) and porcine small intestine mucin isolated from the duodenum (Duo-Mucin) and jejunum (Jej-Mucin) using an exemplary method of the invention. Coomassie Blue Assay stains turquoise the protein domains in mucin. PAS/Schiff assay stains purple the polysaccharide domains in mucin. The reactions with Coomassie blue and PAS demonstrate that mucins isolated from swine intestines using an exemplary method of the invention is very similar to reagent grade porcine stomach mucin obtained from Sigma-Aldrich (St. Louis, Mo.; Cat. No. M1778-10G, Batch No. 064K7005).

Coomassie Blue and PAS/Schiff staining was performed to detect the presence of protein and polysaccharide domains, respectively. These assays showed the presence of both protein and polysaccharide domains in the purified mucin (FIG. 5).

Figure 6:
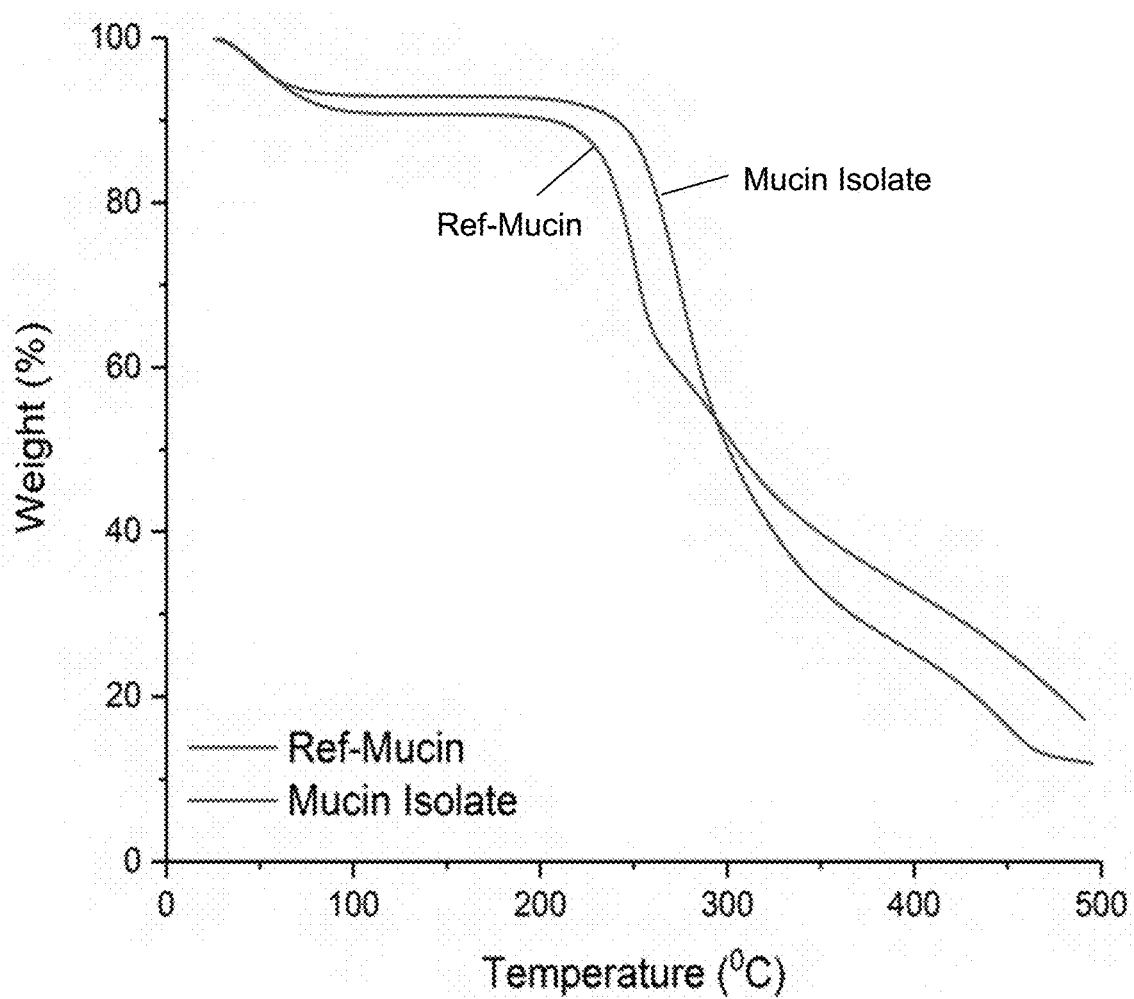
FIG. 6. Thermal gravimetric analysis (TGA) thermogram of commercial porcine stomach mucin (Ref-Mucin) and porcine small intestine mucin isolated (Mucin Isolate) using an exemplary method of the invention.

Thermal gravimetric analysis (TGA) was used to characterize the chemical profile of the purified mucin with thermal analysis (FIG. 6). The purified mucin showed a comparable TGA chemical profile with a standard reference porcine stomach mucin from Sigma-Aldrich (St. Louis, Mo.; Cat. No. M1778-10G, Batch No. 064K7005). Results showed similar weight loss stages. The first one at 50° C. and attributed to the release of water. The second stage at 250° C. is associated with the depolymerization processes. Finally, the third stage at 301° C. for the standard reference porcine stomach mucin and at 446° C. for the mucin isolates is associated with the degradation and decomposition of the material. The difference in the last stage is associated with the higher molecular weight, degree of polymerization, and the extent of crosslinking that differentiates the mucin isolates from the standard reference.

Figure 7:
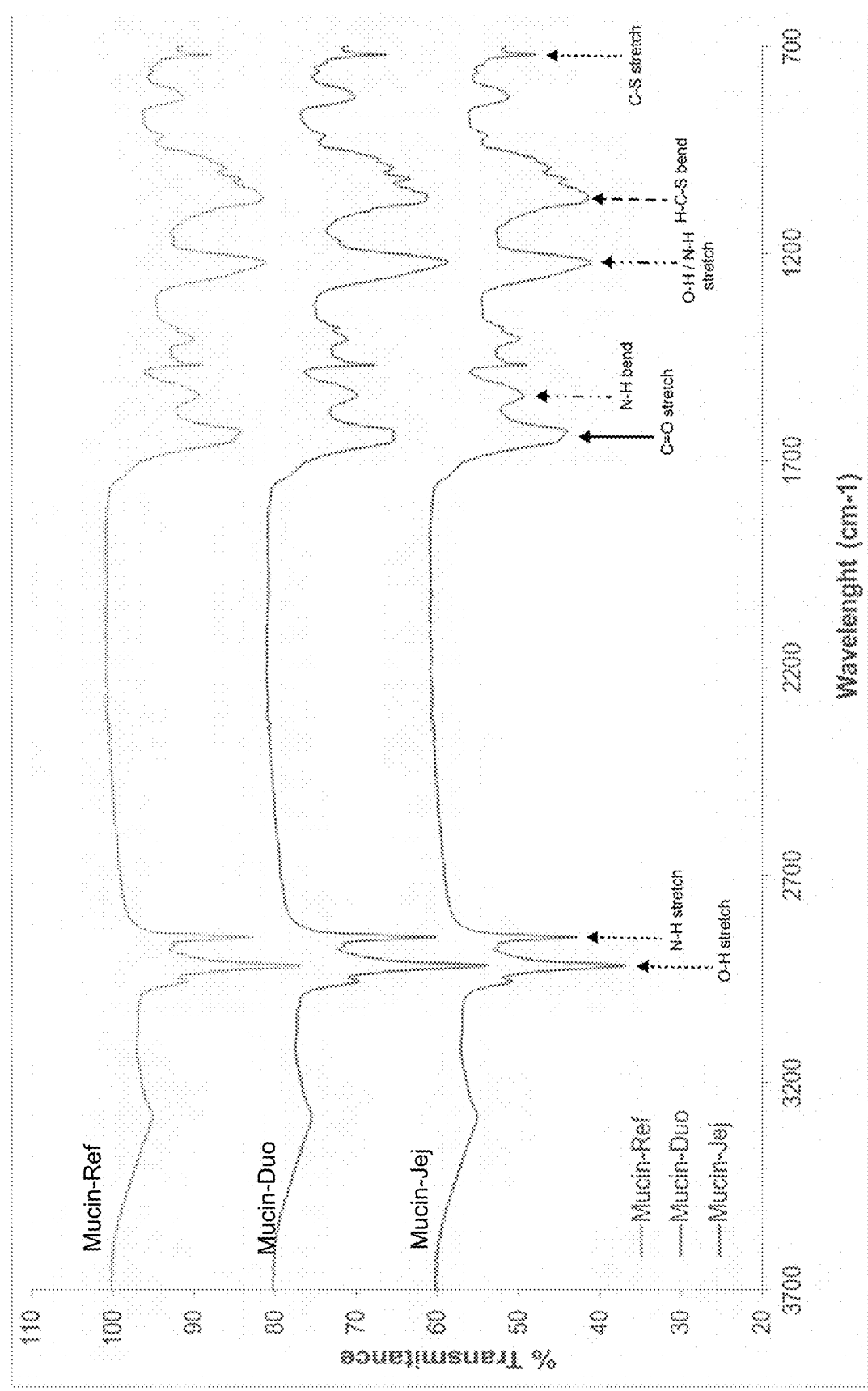
FIG. 7. Fourier transform infrared (FT-IR) spectroscopy analysis showing the chemical characterization of commercial porcine stomach mucin (Ref-Mucin) and porcine small intestine mucin isolated from the duodenum (Mucin-Duo) and jejunum (Mucin-Jej) using an exemplary method of the invention. Principal peaks associated with mucin chemical bonds are marked with arrows. Spectroscopic data was adjusted on the Y-axis so the data does not overlap to facilitate comparative analysis.

Fourier transform infrared (FTIR) spectroscopy analysis of the purified and reference mucin samples is shown in FIG. 7. All the mucin samples showed a similar spectroscopic chemical profile, as suggested by the major transitions associated with characteristic chemical bonds found in mucin structure (indicated with arrows on the spectra). Peaks representing the presence of peptide/protein and polysaccharide domains were present in the spectra of all the mucin samples. Peaks representing the disulfide bonds that bridge individual mucin proteins together to form the macromolecular mucin structures characteristic of MUC2 were also present.

These and other experiments, including gel electrophoresis analysis and proteomics analysis by MALDI-TOF mass spectrometry, show that the mucin purification method described herein succeeds in extracting mucin such as MUC2 from the complex cell and tissue matrix found in porcine small intestines, including duodenum, jejunum, and ilium sections of the small intestine.

Example 5. Mucus Isolation from Intestines

Small intestines from sows were obtained from a processing plant in Watertown, Wis. Intestines were placed on ice and transported to the lab for processing. The intestines were weighed, and the mucus was removed by hand. The mucus was collected into a beaker and weighed to determine yield of mucus per intestine (Table 2).

TABLE 2

Mass of intestines and mucus from 15 porcine intestines.

| Intestine | Mass of intestine before squeezing (g) | Mass of intestine after squeezing (g) | Mass of Mucus (g) |
|---|---|---|---|
| 1 | 623 | 468 | 155 |
| 2 | 894 | 685 | 209 |
| 3 | 1556 | 1122 | 435 |
| 4 | 879 | 702 | 177 |
| 5 | 593 | 464 | 128 |
| 6 | 638 | 536 | 102 |
| 7 | 1567 | 1346 | 222 |
| 8 | 1689 | 1553 | 136 |
| 9 | 1737 | 1541 | 196 |
| 10 | 1269 | 1052 | 216 |
| 11 | 1299 | 1047 | 253 |
| 12 | 1433 | 1321 | 112 |
| 13 | 580 | 540 | 40 |
| 14 | 1562 | 1432 | 130 |
| 15 | 1388 | 1001 | 387 |
| Average | 1181 | 987 | 193 |
| STD | 432 | 397 | 104 |

There was no correlation between intestinal weight and extracted mucus. The variation between the weight of intestines and the mucus extracted may be influenced by the fasted state of the animal prior to slaughter.

Example 6. Variations for Isolating MUC2 from Mucus

The mucus from Example 5 was combined with Mucin Extracting Solution at a ratio of 1:10 (v/v) with continuous mixing at varying times and temperature to determine optimal extraction conditions. After mucus extraction, the solution was filtered through cheesecloth to remove particulate tissue, lipids, and digesta. The filtered material was then centrifuged at varying speeds and for varying times to determine optimal centrifugation parameters. After the initial centrifugation, the supernatant was discarded, and the pellet, which contains MUC2, was washed with varying buffer formulations to determine the optimal conditions for removing the detergent. The hydrated mucus gel was then subjected to freeze-drying (lyophilization) or organic solvent precipitation to determine an optimal method for obtaining MUC2.

Example 6.1. Effect of Acidified Water During the Washing Process on MUC2 Yield The mucus from Example 5 was combined with Mucin Extracting Solution at a ratio of 1:10 (v/v) at room temperature for 1 hour under continuous stirring. The filtered material was centrifuged at 18,000×g for 60 minutes at 4° C. After centrifugation, the supernatant was discarded, and the pellet was re-suspended in 40 mL of double distilled (DD) water or acidified DD water (5 mL of hydrochloric acid 1.995 mL of DD water, final pH 4.00) and centrifugated as before. This process was repeated three times. After the last wash, the pellet was collected, frozen at −20° C., and lyophilized. Table 3 shows the effect of acidified water on the yield of MUC2.

TABLE 3

Effect of the use of acidified water for the washes on MUC2 yield.

| Wash buffer | Wet Mucus (g) | Dry MUC2 (mg) | Dry MUC2 to Wet Mucus (mg/g) | Dry MUC2 per Intestine (mg) |
|---|---|---|---|---|
| DD water | 36.4 | 72.0 | 1.9 | 371.4 |
| Acidified DD water | 45.3 | 110.0 | 2.5 | 483.3 |

The use of acidified DD water increased the yield of MUC2 from 1.9 to 2.5 mg of dry MUC2 per g of wet mucus.

Example 6.2 Effect of Centrifugal Force During the Separation Process

The mucus from Example 5 was combined with Mucin Extracting Solution at a ratio of 1:10 (v/v) at room temperature for 1 hour under continuous stirring. The filtered material was centrifuged at variable centrifugal forces (11,000, 18,000, 30,000×g) for 60 minutes at 4° C. After centrifugation, the supernatant was discarded, and the pellet was re-suspended in 40 mL of acidified DD water and centrifugated as before. This process was repeated three times. After the last wash, the pellet was collected, frozen at −20° C., and lyophilized. Results are shown in Table 4

TABLE 4

Effect of the centrifugal force on the mg of dry MUC2 per g of wet mucus.

| Centrifugal Force (x g) | Wet Mucus (g) | Dry MUC2 (mg) | Dry MUC2 to Wet Mucus (mg/g) | Dry MUC2 per Intestine (mg) |
|---|---|---|---|---|
| 11,000 | 38.7 | 50.0 | 1.3 | 249.8 |
| 18,000 | 36.4 | 72.4 | 1.9 | 371.4 |
| 30,000 | 56.7 | 182.8 | 3.0 | 580.0 |

Increasing the centrifugal force during the wash steps increased the yield of MUC2 from 1.3 to 3.0 mg of dry MUC2 per g of wet mucus.

Example 6.3. Effect of Organic Solvent Precipitation Vs. Lyophilization for Drying and Removal of Residual Detergent The mucus from Example 5 was combined with Mucin Extracting Solution at a ratio of 1:10 (v/v) at room temperature for 1 hour under continuous stirring. The filtered material was centrifuged at 30,000×g for 60 minutes at 4° C. After centrifugation, the supernatant was carefully decanted and discarded. The pellet was composed of two fractions, a dense fraction at the bottom of the centrifuge tube and a dispersed gel fraction that was free flowing. The dense fraction is primarily composed of tissue, sodium laurel sulfate (SLS), and lipids. The gel fraction contains mucin. The dense fraction of the pellet was carefully removed and discarded, and the gel was collected for further rinsing with acidified DD water and centrifugated as before. This process was repeated three times. Centrifugation resulted in a dense and gel fraction. There was residual SLS in both the dense fraction and the gel fraction after the first wash. The amount of dense fraction decreased after each wash. The washing removed SLS from the gel, and, after the final wash, there were trace levels of SLS remaining. After the final wash, the pellet was primarily composed of a gel and was collected and either lyophilized (freeze dried) or precipitated with absolute acetone (100 mL of the recovered gel was mixed with 300 mL of absolute acetone and then filtered using a Buchner funnel) prior to air drying. The dried MUC2 was then analyzed for the presence of residual detergent via a modified colorimetric method.

The remaining sodium laurel sulfate (SLS) in the MUC2 isolates was measured using the colorimetric method of Arand et al. 1992 (Arand, M., Friedberg, T., & Oesch, F. (1992). Colorimetric quantitation of trace amounts of sodium lauryl sulfate in the presence of nucleic acids and proteins. *Analytical biochemistry*, 207(1), 73-75). Six hundred microliters of MUC2 isolates at a concentration of 1 mg/mL was mixed with 600 µL of methylene blue reagent (0.67 mM methylene blue, 0.35 mM $Na_2SO_4$, and 0.17 mM $H_2SO_4$). Then, 2.4 mL of chloroform was added to initiate a phase separation. The lower organic phase was transferred to a quartz cuvette using a Pasteur pipette and the absorbance was determined at 651 nm. A SLS standard curve from 1 to 15 µg/mL was prepared for quantification. Results are shown in Table 5.

TABLE 5

Effect of the use of acetone precipitation on the mg of SLS per g of dry MUC2.

| MUC2 Drying Process | Wet Mucus (g) | Dry MUC2 (mg) | SLS to dry MUC2 (mg/g) | Dry MUC2 to Wet Mucus (mg/g) | Dry MUC2 per Intestine (mg) |
|---|---|---|---|---|---|
| Lyophilization | 65.6 | 146.0 | 120.2 | 2.2 | 425.3 |
| Acetone precipitation | 57.3 | 167.9 | 2.6 | 2.9 | 560.6 |

A reduction in SLS from the dried MUC2 was achieved with acetone precipitation. The acetone dehydrates the MUC2 gel and thus removes the water and residual SLS entrapped within the gel matrix. In addition, the precipitation with acetone dries the material faster (hours vs days) than freeze-drying. Eliminating the freeze-drying process improves efficiency.

Example 6.4. Effect of Temperature of Mucin Extracting Solution and Extraction Time During the Extraction Process The mucus from Example 5 was combined with the Mucin Extracting Solution at a ratio of 1:10 (v/v) at room temperature, 60° C., or 100° C. for 1 hour under continuous stirring. In addition, time under continuous stirring was also evaluated. Extraction, centrifugation, and rinsing where done as described in Example 6.3. After the last wash, the centrifugate was collected, frozen at −20° C., and lyophilized or precipitated with acetone. Results are shown in Tables 6.

TABLE 6

Sample preparations and isolation conditions.

| Sample | Extraction Temperature | Dry Method | Extraction Time (min) | Centrifugal Force (x g) | SLS to Dry MUC2 (mg/g) |
|---|---|---|---|---|---|
| 1 | RT | Lyophilization | 60 | 30,000 | 120.2 |
| 2 | RT | Acetone precipitation | 60 | 30,000 | n/a |
| 3 | RT | Acetone precipitation | 60 | 30,000 | 1.3 |
| 4 | 60° C. | Acetone precipitation | 60 | 30,000 | 0.1 |
| 5 | 100° C. | Acetone precipitation | 60 | 30,000 | 1.7 |
| 6 | 60° C. | Acetone precipitation | 5 | 30,000 | 1.3 |
| 7 | 60° C. | Acetone precipitation | 10 | 30,000 | 0.8 |
| 8 | 60° C. | Acetone precipitation | 20 | 30,000 | 0.8 |
| 9 | Control | Control | Control | | |
| 10 | RT | Lyophilization | 60 | 18,000 | 519.3 |
| 11 | RT | Lyophilization | 60 | 18,000 | 250.7 |
| 12 | RT | Acetone precipitation | 5 | 30,000 | 1.7 |
| 13 | RT | Acetone precipitation | 10 | 30,000 | 1.4 |
| 14 | RT | Acetone precipitation | 20 | 30,000 | 1.1 |
| 15 | RT | Acetone precipitation | 30 | 30,000 | 2.5 |

The mucus from Example 5 was combined with the Mucin Extracting Solution at a ratio of 1:10 (v/v) to test the effect of the extraction temperature on the yield of MUC2. The extraction of the material was done at room temperature, 60° C., or 100° C. for 1 hour under continuous stirring. The filtered material was centrifuged at 30,000×g for 20 minutes at 4° C. After centrifugation, the supernatant was carefully decanted and discarded. The gel was collected for further rinsing with acidified DD water and centrifuged as before. This process was repeated three times. After the final wash, the gel was collected and precipitated with absolute acetone. Results in Table 7 show the effect of the extraction temperature on MUC2 yield. There is a decrease in the yield of MUC2 when extraction occurs at either 60° or 100° C.

TABLE 7

Effect of Extraction Temperature on MUC2 yield.

| Extraction Temperature | Wet Mucus (g) | Dry MUC2 (mg) | Dry MUC2 to Wet Mucus (mg/g) | Dry MUC2 per Intestine (mg) |
|---|---|---|---|---|
| ~25° C. | 53.5 | 145.5 | 2.7 | 525.9 |
| 60° C. | 51.0 | 116.6 | 2.3 | 444.7 |
| 100° C. | 54.4 | 20.2 | 0.4 | 77.3 |

Figure 8:
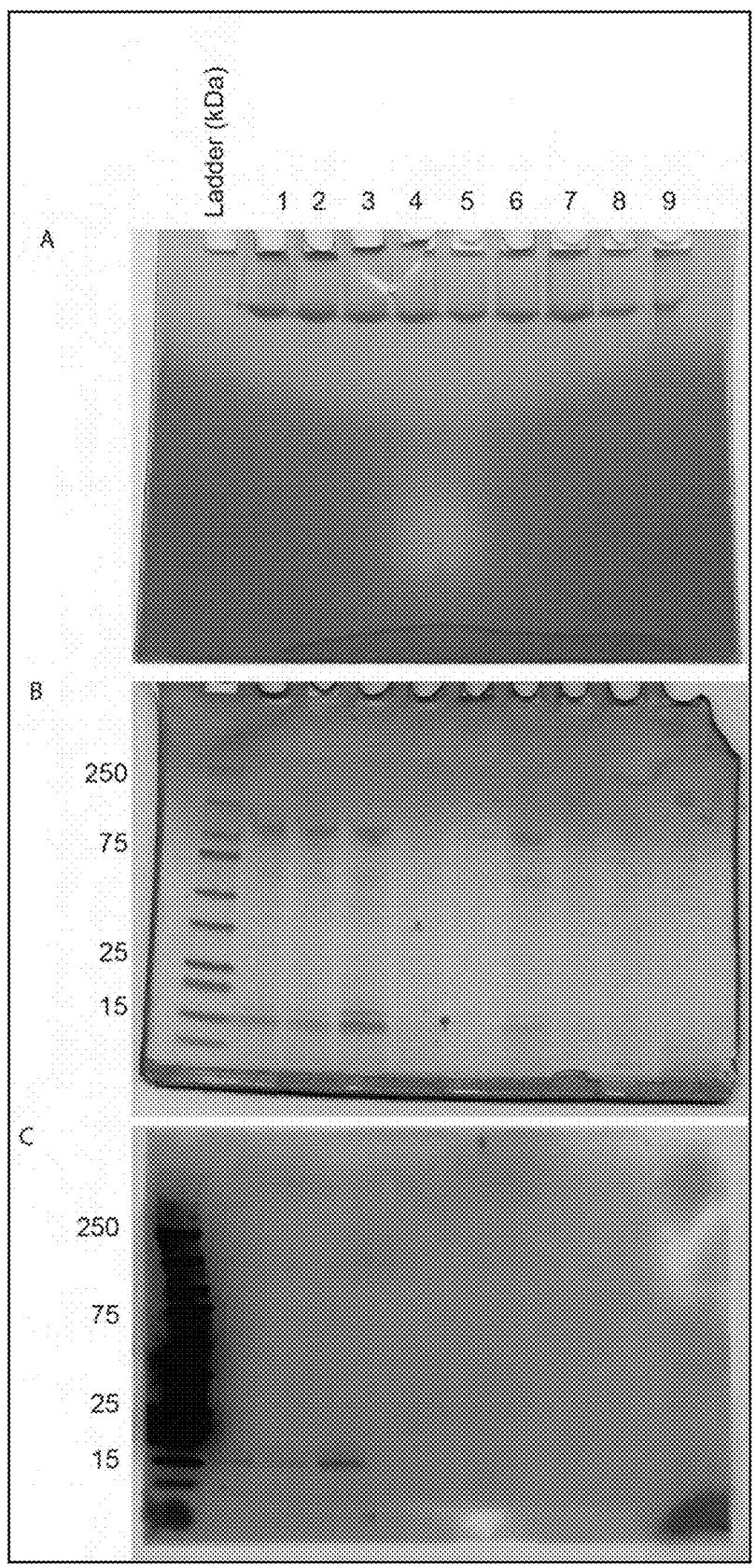
FIG. 8 shows a PAS glycoprotein stain (panel A), SimplyBlue protein stain (panel B), and Western Blot analysis (panel C) of MUC2 isolates run on gels. The numbers above each lane in panel A refer to the samples as identified in Table 6 and are the same for each of panels A, B, and C. The numbers to the left of panels B and C refer to molecular weights in kDa.
Figure 9:
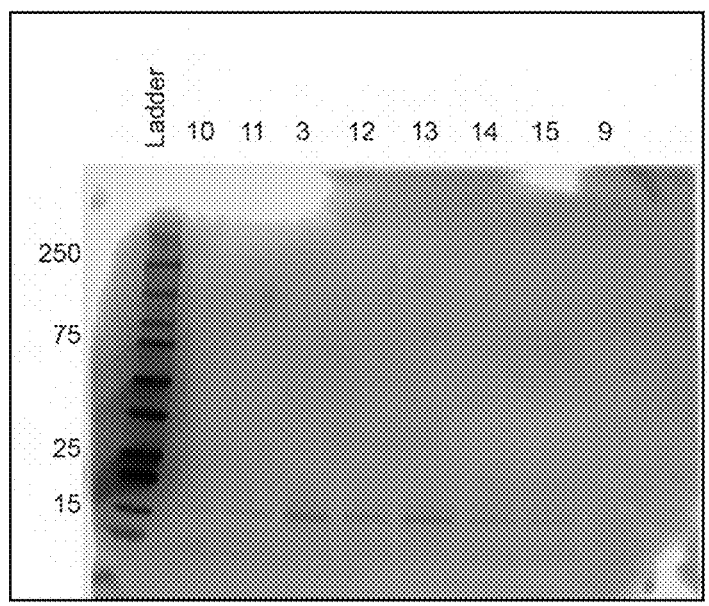
FIG. 9 shows a Western Blot analysis of MUC2 isolates prepared with varying room temperature extraction times. The numbers above each lane refer to the samples as identified in Table 6.

The MUC2 isolates represented in Table 6 were evaluated for purity using SDS-PAGE gel electrophoresis with various stains and western blotting. The isolates were suspended in water to obtain a concentration of 1 mg/mL. Samples were then combined with equal volume of Sample Buffer containing 355 mM of 2-mercaptoethanol as a reducing agent and heated at 100° C. for 10 minutes prior to loading into a 4-20% TGX mini gel (Bio-Rad). Porcine stomach mucin (Sigma) was used for comparison purposes. Gels were run at 200 volts for 35 minutes. After the gels ran to completion, gels were removed and washed with DD water. Separate gels were stained with periodic acid-Schiff (PAS) reagent to identify the presence of glycoproteins (FIG. 8, panel A) and with SimplyBlue Safe Stain to identify the presence of proteins (FIG. 8, panel B). Another gel was transferred to PVDF membrane and incubated for 1 hour with SuperBlock TBS-T (Thermo Fisher). The membrane was incubated overnight (ON) with α-MUC2 (1:10,000) antibody (Santa Cruz Biotech). After washing, membranes were incubated for 1 h with the corresponding HRP-labeled secondary antibodies (1:10,000). Protein bands were visualized by chemiluminescence using the LiCOR WesternSure ECL kit (LiCOR) and the c-DiGit blot scanner (LiCOR) (FIG. 8, panel C; FIG. 9).

FIG. 8 illustrates the effect of extraction temperature and time on the purity of isolated MUC2. Panel A of FIG. 8 confirms that all samples had a glycoprotein component. Panel B of FIG. 8 illustrates the purity of the isolated samples as only one or two protein bands can be identified. In addition, panel B of FIG. 8 indicates that heating during the extraction process reduces the protein content in the MUC2 isolates. This is made evident by the loss of blue stain observed in samples 4-8 when compared to sample 3. Panel C of FIG. 8 shows that the only α-MUC2-reactive samples are samples 1-3, which were not exposed to heat during the extraction process.

MUC2 is a high-molecular-weight glycoprotein with many oligosaccharide side chains attached to a protein core rich in proline, threonine, and serine (PTS domain) by O-glycosidic linkages. Combined within the PTS domain, there are cysteine-rich (Cys) domains, which are domains for the formation of non-covalent cross-linkages via disulfide bonds. These Cys domains have an important role in the assembly and gelation properties of MUC2. Disulfide bonds undergo degradation at temperatures over 90° C. causing irreversible loss of enzymatic activity, or in the case of MUC2, loss of gelation properties. We hypothesize that this causes a decrease in the size of the MUC2 gel after the centrifugation and a decrease in the yield of MUC2 gel as the temperature increases. We hypothesize that the decrease in MUC2 yield can be attributed to the thermal degradation of disulfide bonds in the Cys domains and loss of the gel formation properties of the MUC2 during heated extraction.

FIG. 9 illustrates the effect of extraction time and centrifugal force on the purity of isolated MUC2. The preparation of these MUC2 isolates are summarized in Table 6.

Example 6.5. Analysis and Estimation of MUC2 in Mucus

Figure 10:
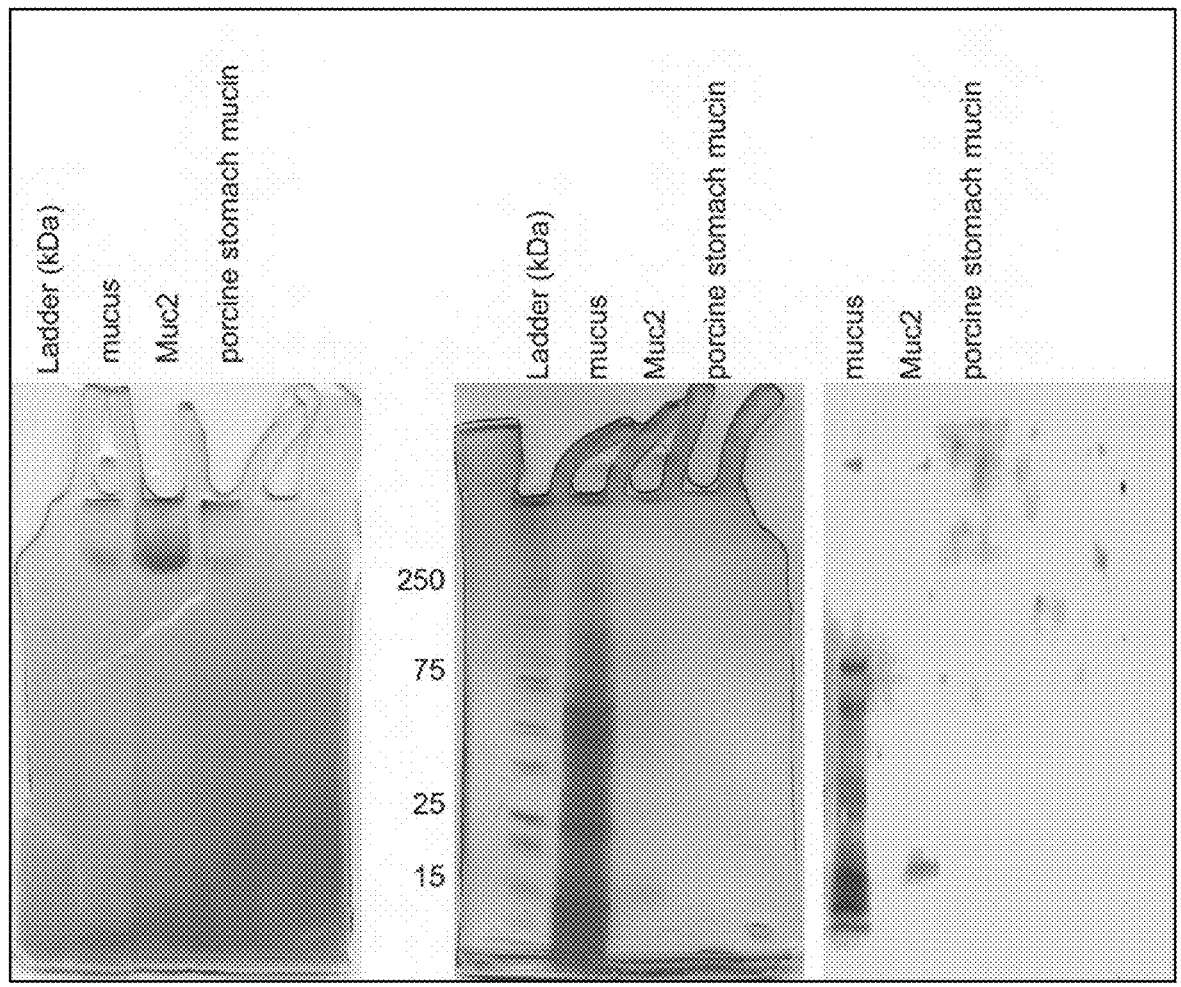
FIG. 10 shows a PAS glycoprotein stain (left), SimplyBlue protein stain (middle), and Western Blot analysis (right) of raw mucus, MUC2 isolated from mucus, and porcine stomach mucin.

The extracted mucus was analyzed for total protein content using the BCA Protein Assay (Thermo) and bovine serum albumin (BSA) as a standard. The extracted mucus contains 20.71 mg BSA/mL total protein. The extracted mucus and purified MUC2 was evaluated via SDS-PAGE in combination with staining or Western Blotting as described above for FIGS. 8 and 9 to determine the extraction efficiency of the extraction and isolation procedure. FIG. 10 shows that the process successfully separates MUC2 from mucus, resulting in a purified material.

Example 7. Applications with Purified Mucin

Purified gastric mucins are currently used for a wide range of applications, including model systems for native mucus, lubricants, or antiviral/antibacterial supplements. However, commercially available porcine gastric mucins do not exhibit gel-forming properties and show greatly reduced anti-viral/anti-bacterial activity. Therefore, purified native small intestine mucin such as MUC2 has great potential to act as new biological material for nutritional and biomedical applications.

The MUC2 central protein backbone contains hydrophobic and charged domains, while the mucin-associated glycans provide hydrogen bonding capabilities, high hydration, and negative charges. Mucins such as MUC2 can be used as functional surface coatings, mucin-based auxiliaries during minimally invasive surgery, and sustained drug delivery by mucin-assembled hydrogels. The biochemical versatility of MUC2 represents potential binding sites for certain drugs and a suitable gel-like environment for cell culture. If assembled into hydrogels, mucins can prevent drugs from freely diffusing out for sustained delivery. *Akkermansia muciniphilia* is a probiotic bacterium that is associated with decreased risk of obesity, diabetes, inflammation and metabolic disorders. As the species name implies, *Akkermansia muciniphilia* uses mucin as its main substrate for growth. Therefore, mucin can be used as prebiotic in a blend with *Akkermansia muciniphilia* for nutritional and medicinal food applications.

Figure 11:
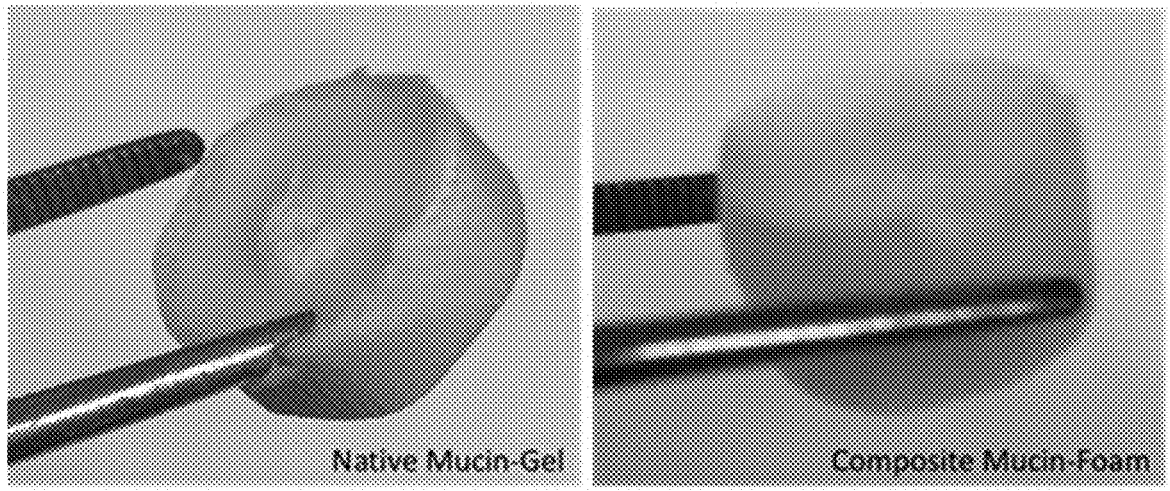
FIG. 11. Illustrative images showing the physical appearance of a native mucin gel (left) and a mucin-chitosan (1:1) (mass mucin:mass chitosan) composite foam (right) fabricated with mucin samples isolated from porcine small intestine sections using an exemplary method of the invention.

We fabricated mucin-based biomaterial prototypes in the form of native mucin gels and composite mucin foams (FIG. 11) with the purified mucin of the invention. These gels and foams have use in such applications as drug delivery, surface coating, wound healing, and tissue engineering, among others. The mucin gels were obtained by dispersing the purified mucin (MUC2) in acetic acid (0.1 M), placing the dispersion in a glass mold, and letting it dry at room temperature until a viscous gel material was casted. The composite mucin foams were obtained by mixing purified mucin (MUC2) dispersed in a chitosan solution (1 mg/mL) in acetic acid (0.1 M) under gentle stirring for 30 minutes. Mixture of mucin-chitosan (1:1) (mass mucin:mass chitosan) was casted into silicone molds and freeze dried for obtaining a foam-like material.

Figure 12:
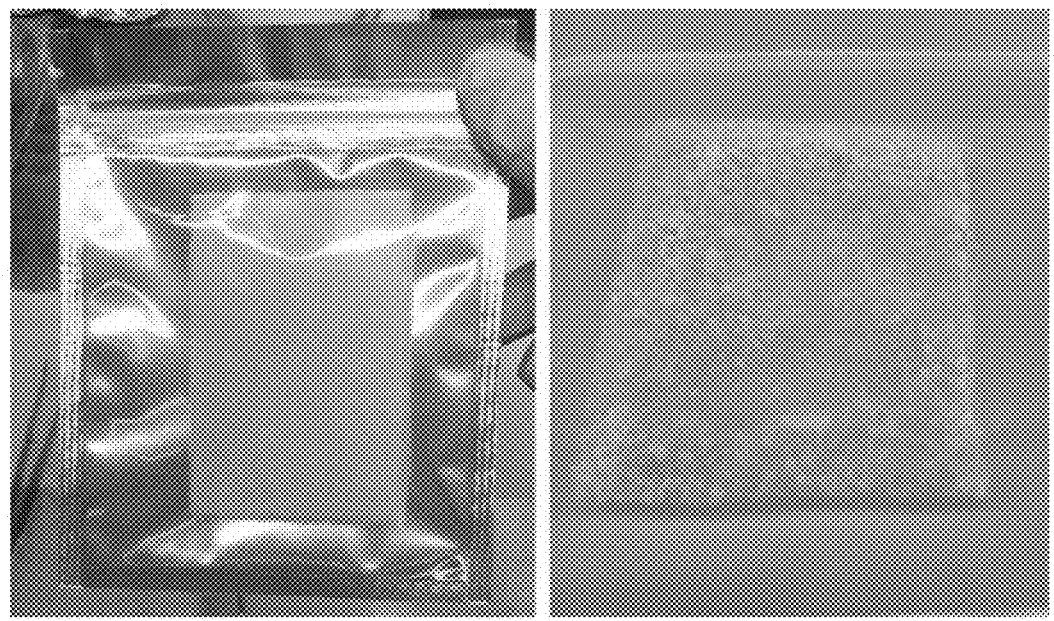
FIG. 12. Photographs showing the physical appearance of a mucin-based wound dressing template (left) and its behavior under media conditions (right), showing suitable mechanical performance, swelling properties, and degradation rates to be applied in wound management.

We also used the purified mucin of the invention to make mucin-based films. To make one type of film, we mixed the purified mucin with chitosan biopolymer at different weight ratios and subjected the mixture to freeze drying and thermal crosslinking to yield 3D sponge-like films. The mucin films were obtained by the freeze-drying technique as explained above. The mucin foams were obtained after freeze drying and were further thermally crosslinked in a vacuum oven at 20 mbar and 120° C. for 12 hours to increase the mucin foam's mechanical and chemical stability. These generated films can be used as wound dressings for applications in wound management, as shown in FIG. 12.

The films were tested for behavior under media conditions, including mechanical performance, swelling properties, and degradation rates. After thermal crosslinking, the mucin films were placed in phosphate buffer solution (pH 7.2) at 25° C. and let to swell under gentle shaking until full physical degradation was observed. Thermally crosslinked mucin films were stable over a 30-day period, not showing any evidence of physical degradation (FIG. 12, right panel). The films therefore showed mechanical performance, swelling properties, and degradation rates under media conditions suitable for applications in wound management.

The purified mucin of the invention is extremely hygroscopic. It can accordingly be used as an absorbent material in, for example, diapers or any other item requiring moisture absorbance. In one embodiment, the purified mucin of the invention can be applied as a solid, dry powder to a wound to stop bleeding and/or close or sealing the wound.

The purified mucin of the invention is lubricious once hydrated. It can accordingly be employed as a surface coating on any device requiring a lubricious surface. Such devices include medical devices such as stents, catheters, or other medical devices.

In its various solid or semi-solid forms (e.g., gels, foams, etc.), the purified mucin of the invention can be used as a replacement or in combination with agar or agarose as a medium for the growth of microorganisms; a solid phase for chromatography, electrophoresis, or other types of separation; or other uses.

The mucin purification procedure described herein facilitates native mucin isolation from different tissue samples, and the mucin purified therewith is suitable for applications in medical diagnosis, basic and applied research, and biomedical applications, among others.

We claim:

1. A method of purifying mucin from a mucin-containing substance comprising:
   combining the mucin-containing substance with water, a surfactant, a chelating agent, and a protic solvent to form a purification mixture:
   incubating the purification mixture for a time sufficient to form a mucin precipitate in a liquid phase; and
   separating the mucin precipitate from the liquid phase, wherein the mucin precipitate comprises the mucin.

2. A method of purifying mucin from a mucin-containing substance comprising:
   combining the mucin-containing substance with water and more than one purification agent selected from the group consisting of a surfactant, a chelating agent, and a protic solvent to form a purification mixture, wherein the surfactant comprises at least one of an anionic surfactant, a nonionic surfactant, and a zwitterionic surfactant;
   incubating the purification mixture for a time sufficient to form a mucin precipitate in a liquid phase; and
   separating the mucin precipitate from the liquid phase, wherein the mucin precipitate comprises the mucin,
   wherein the combining comprises combining the mucin-containing substance with the water, the surfactant, and the chelating agent.

3. The method of claim 2, wherein the incubating is conducted at a temperature of about 0-90° C.

4. The method of claim 2, wherein:
   the surfactant comprises an anionic surfactant;
   the chelating agent comprises at least one of ethylenediaminetetraacetic acid, disodium ethylenediaminetetraacetate dehydrate, nitriloacetic acid, and diethylenetriamine pentaacetic acid;
   the protic solvent comprises an alcohol; and
   the mucin-containing substance comprises mucus.

5. The method of claim 2, wherein the combining comprises combining the mucin-containing substance with a purification solution comprising the water and the more than one purification agent selected from the group consisting of the surfactant, the chelating agent, and the protic solvent.

6. The method of claim 5, wherein the purification solution comprises the water, the surfactant, the chelating agent, and the protic solvent.

7. The method of claim 5, wherein the purification solution has a pH from about 6 to about 8 and comprises:
   the surfactant in an amount of about 0.3-10% w/v;
   the chelating agent in an amount of about 0.3-6% w/v; and
   the water in an amount greater than about 90% v/v.

8. The method of claim 5, wherein the combining comprises combining the mucin-containing substance with the purification solution in a volume ratio of from about 50:1 to about 1:50 (vol. mucin-containing substance:vol. purification solution).

9. The method of claim 2, wherein the separating comprises:
   centrifuging the mucin precipitate in the liquid phase to form a mucin precipitate pellet comprising the mucin precipitate and a liquid phase supernatant; and
   removing the liquid phase supernatant from the mucin precipitate pellet.

10. The method of claim 9, wherein the mucin precipitate pellet comprises a first fraction and a second fraction, the first fraction is denser than the second fraction, the second fraction comprises the mucin precipitate, and the method further comprises separating the first fraction from the second fraction.

11. The method of claim 2, further comprising, after the separating, washing the mucin precipitate with an acidic wash solution having a pH of about 2-6.

12. The method of claim 2, further comprising, after the separating, washing the mucin precipitate with an organic solvent.

13. The method of claim 2, further comprising, after the separating, drying the mucin precipitate.

14. The method of claim 13, wherein the dying comprises freeze-drying the mucin precipitate.

15. A purified mucin prepared according to claim 2.

16. A material comprising the purified mucin of claim 15.

17. The material of claim 16, wherein the material is in the form of a gel, a foam, a film, or a powder.

18. The material of claim 16, wherein the material further comprises a biopolymer.

19. The material of claim 16, wherein the material further comprises a biopolymer selected from the group consisting of a tannin and chitosan.

20. The method of claim 2, wherein the mucin-containing substance comprises mucus from at least one of a respiratory system and a gastrointestinal system of an animal.

21. The method of claim 2, wherein the mucin-containing substance comprises mucus from at least one of lungs and intestines of an animal.

22. The method of claim 2, wherein the mucin comprises mucin 2.

23. The method of claim 2, wherein the surfactant comprises an anionic surfactant.

* * * * *